United States Patent [19]

Lower

[11] Patent Number: 4,612,920

[45] Date of Patent: Sep. 23, 1986

[54] COMPRESSION HIP SCREW

[75] Inventor: Jerry L. Lower, Bourbon, Ind.

[73] Assignee: Zimmer, Inc., Warsaw, Ind.

[21] Appl. No.: 668,782

[22] Filed: Nov. 6, 1984

[51] Int. Cl.$^4$ .............................................. A61F 5/04
[52] U.S. Cl. ................................................ 128/92 BA
[58] Field of Search ........... 128/92 B, 92 BA, 92 BB, 128/92 D

[56] References Cited

U.S. PATENT DOCUMENTS

| | | | |
|---|---|---|---|
| 1,814,858 | 7/1931 | Rutter | 411/110 |
| 2,557,669 | 6/1951 | Lloyd | 128/92 |
| 2,612,159 | 9/1952 | Collison | 128/92 BA |
| 2,621,653 | 12/1952 | Briggs | 128/92 |
| 2,628,614 | 2/1953 | Briggs | 128/92 |
| 2,682,265 | 6/1954 | Collison | 128/92 |
| 2,702,543 | 2/1955 | Pugh et al. | 128/92 |
| 2,708,144 | 5/1955 | Carr | 309/17 |
| 2,834,342 | 5/1958 | Yost | 128/92 |
| 2,937,642 | 5/1960 | Lang et al. | 128/92 |
| 3,029,811 | 4/1962 | Yost | 128/92 BA |
| 3,206,236 | 9/1965 | Darling | 287/52.05 |
| 3,530,854 | 9/1979 | Kearney | 128/92 BA |
| 3,561,437 | 2/1971 | Orlich | 128/92 |
| 3,616,829 | 11/1971 | Runton | 151/23 |
| 3,695,259 | 10/1972 | Yost | 128/92 |
| 3,996,931 | 12/1976 | Callender, Jr. | 128/92 |
| 4,095,591 | 6/1978 | Graham, Jr. et al. | 128/92 |
| 4,172,452 | 11/1979 | Forte et al. | 128/92 |
| 4,364,382 | 12/1982 | Mennen | 128/92 |
| 4,429,690 | 2/1984 | Angelino-Pievani | 128/92 |
| 4,432,358 | 2/1984 | Fixel | 128/92 |
| 4,438,762 | 3/1984 | Kyle | 128/92 |
| 4,441,492 | 4/1984 | Rydell et al. | 128/92 BA |
| 4,530,355 | 7/1985 | Griggs | 128/92 |

Primary Examiner—Gene Mancene
Assistant Examiner—Wenceslao J. Contreras
Attorney, Agent, or Firm—Paul David Schoenle

[57] ABSTRACT

A compression hip screw comprises a plate with a barrel, a lag screw adapted for fixation to a femoral head, a compression screw engageable with the lag screw to retain the plate and barrel attached with the femur and a locking pin to oppose rotation between the barrel and the lag screw. The locking pin is disposed on one side of the barrel to provide a robust structure for the lag screw and enable the barrel to transmit loads developed during the walking mode for the hip.

12 Claims, 4 Drawing Figures

U.S. Patent   Sep. 23, 1986   4,612,920
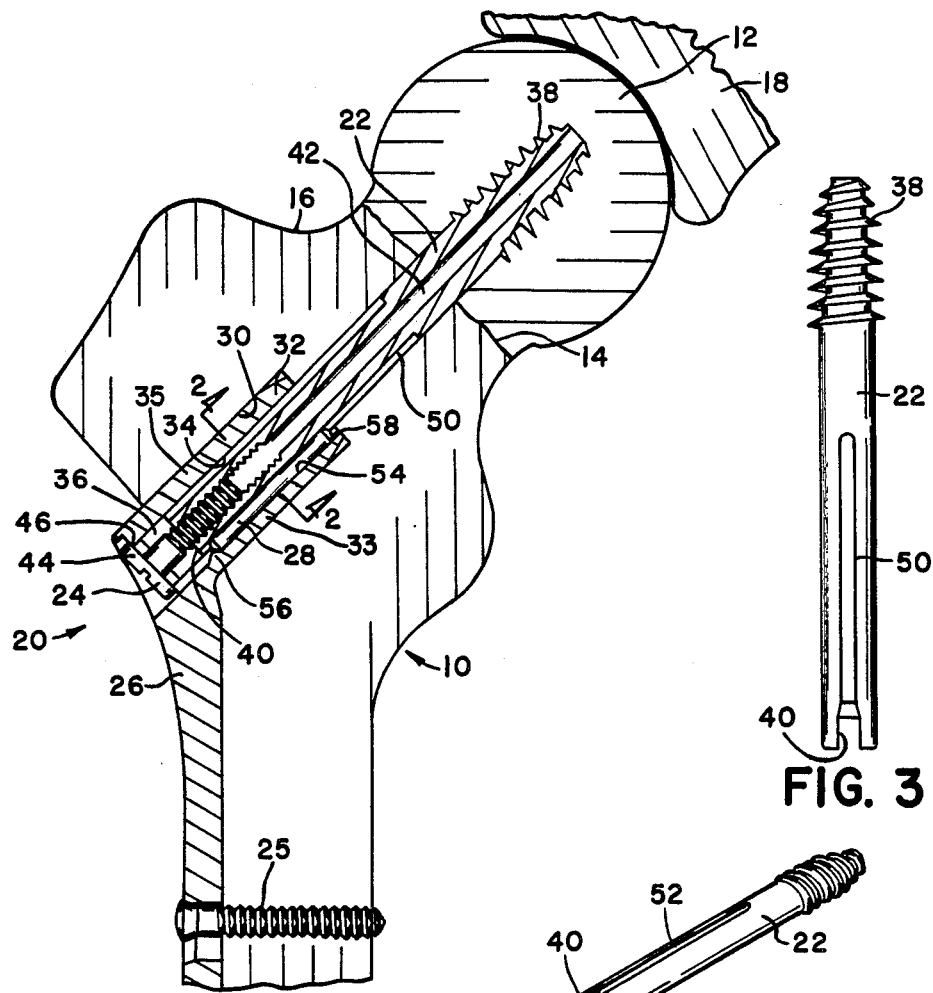
FIG. 1
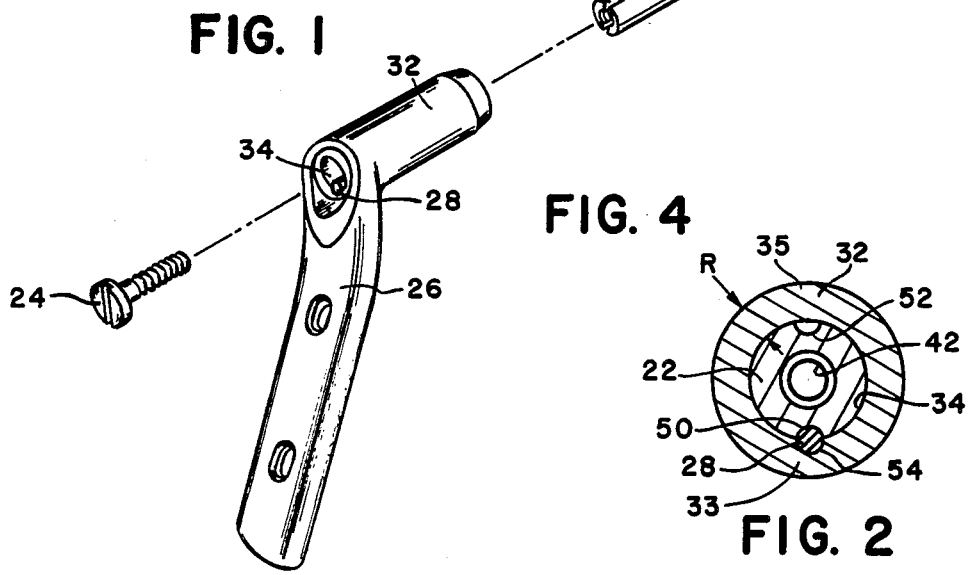
FIG. 3
FIG. 4
FIG. 2

COMPRESSION HIP SCREW

This invention relates to a compression hip screw which rigidly connects a femoral head to the remaining portion of the femur despite a fracture in the area of the femur neck.

Heretofore, a compression hip screw provided a lag screw extending through the femur and into the femoral head. An opening was drilled through the femur from an opposite side of the femoral head to receive the lag screw. With the lag screw threadably coupled to the femoral head, a plate was disposed adjacent the femur so that a barrel formed by the plate extended into the opening. The lag screw extended into a bore formed by the barrel so that a compression screw or bolt could threadably engage the lag screw and oppose the barrel to bias the femoral head in the direction of the fracture to take up any spacing at the fracture.

As shown in U.S. Pat. No. 4,432,358 issued Feb. 21, 1984 to Fixel, it is known that a locking assembly can be provided to a keyless assembly to prevent rotation of the lag screw relative to the plate and barrel. In order to accommodate the locking assembly, the barrel is modified to provide additional holes and the lag screw is modified to define a hexagonal hole to receive the locking assembly, which is longer than the lag screw.

During a normal walking cycle for the femur and compression hip screw, the superior side of the barrel is loaded in tension and the inferior side of the barrel is loaded in compression. With the substantial loads imparted to the plate and barrel it is desirable to reduce the possibility of failure. Therefore, if any part of the compression hip screw should fail, it may be necessary for the patient to undergo additional surgery. For this reason, the lag screw and barrel should be designed for optimum load transfer.

The present invention comprises a compression hip screw with a locking device or assembly that is disposed between the lag screw and the barrel on the inferior side of the barrel so that a uniform profile is retained for the superior side of the barrel. The locking device comprises a pin disposed in a groove formed by the barrel and a recess formed by the lag screw.

It is an advantage of the present invention that a compression hip screw can be modified slightly to accommodate a locking assembly without substantially reducing the load carrying capability of the compression hip screw. In the drawings, FIG. 1 depicts the compression hip screw in cross section as applied to a femur having a fracture at the neck thereof.

FIG. 2 is a cross sectional view taken along line 2—2 of FIG 1.

FIG. 3 is a side view of the lag screw.

FIG. 4 is an exploded view of the compression screw, barrel and lag screw.

A femur 10 is shown in FIG. 1 with a femoral head 12 and a fracture 14 located at a neck 16. The femoral head 12 forms a hip joint with an acetabular member 18.

A compression hip screw 20 includes a lag screw 22, a compression screw 24 threadably coupled to the lag screw 22, a plate 26 adapted for attachment to the femur via bone screws 25, and a locking pin 28. An opening 30 is formed in the femur to extend from a lateral side of the femur to an internal position within the femoral head. The plate 26 defines an integral barrel 32 disposed in the opening 30. The barrel is formed with a bore 34 extending therethrough. A first end 36 of the lag screw is disposed in the bore 34 when a second threaded end 38 is threaded into the femoral head for fixation therewith. The first end 36 is slotted at 40 so that a screwdriver or the like can be utilized to advance the lag screw into the femoral head. A passage 42 within the lag screw 22 is provided with a threaded internal surface at the first end so that the compression screw 24 is engageable therewith. The compression screw 24 forms a flange 44 which abuts a shoulder 46 on the barrel 32 when the compression screw 24 is fully engaged with the lag screw 22.

In accordance with the invention, the lag screw is provided with a pair of recesses 50 and 52 and the barrel 32 is provided with a groove 54. The pair of recesses 50 and 52 are disposed on opposite sides of the lag screw while the groove 54 is disposed on the inferior side 33 of the barrel. As a result the superior side 35 of the barrel 32, viewing FIGS. 1 and 2, defines a uniform cylindrical profile with a constant radial thickness R. The pin 28 fits within the groove 54 and extends into the bore 34 to also fit within one of the recesses 50 or 52. Preferably, the groove 54 is dimensioned to receive 75% of the pin's diameter and the pair of recesses is dimensioned to receive 25% of the pin's diameter. In order to retain the pin 28 longitudinally in the groove 54, a pair of projections 56 and 58 are formed at the ends of the groove 54. The pair of projections form a slight interference with the pin so that the pin can be forced onto the groove but the pin will not freely withdraw from the groove. Therefore, the pin is yieldably retained in the groove. The wall of the groove 54 partially overlaps the diameter of the pin 28 to prevent radially withdrawal thereof.

The technique described hereinafter is one way to attach the compression hip screw 20 to the femur 10. Other techniques are feasible in view of orthopaedic surgeon preferences and the characteristics of the femur fracture. The opening 30 is provided by a suitable tool, such as a reamer. The lag screw 22 is secured to the femoral head 12 via the opening 30 by rotating the lag screw 22 for advancement in the opening 30 to a predetermined location. For a "keyed" insertion, the pin 28 is disposed in the groove 54 and the barrel 32 is aligned with the lag screw 22 for insertion of the latter in bore 34. If the recesses 50 or 52 are not aligned with pin 28, the barrel 32 and plate 26 are rotated until the pin 28 is free to advance into either recess. With the barrel fully disposed in the opening 30, the plate 26 and barrel 32 are rotated to further secure the lag screw 22 into the femoral head 12. When the plate is adjacent the femur, the bone screws 25 are fastened to the femur to fixedly attach the plate thereto. Thereafter the compression screw 24 is threadably coupled to the lag screw 22 so that the femoral head 12 is biased in compression toward the barrel 32 to eliminate or reduce any spacing at the fracture 14. Alternatively, the compression screw 24 can be secured before the bone screw 25 is fastened to the femur. For a "keyless" insertion, the barrel 32 is advanced into the opening 30 over the lag screw without the pin 28 in the groove 54. With the barrel 32 in the opening 30, the plate 26 and barrel 32 are rotated until the groove 54 is aligned with either recess 50 or 52. The pin 28 is then inserted into the groove 54 and one of the recesses to prevent rotation between the barrel 32 and the lag screw 22. Thereafter, the barrel 32 and plate 26 are rotated to further secure the lag screw 22 to the femoral head 12 and align the plate 26 with the femur 10.

Although the foregoing description proposes use of the pin 28, it is possible to utilize the lag screw 22, the compression screw 24, the plate 26, and the barrel 32 in the absence of the pin 28, should the orthopaedic surgeon prefer a "keyless" compression hip screw. If the orthopaedic surgeon elects to omit the pin 28, the structure for the barrel 32 and lag screw 22 retains the uniform cylindrical profile of constant radial thickness for the barrel 32 so that the tension loads imparted to the barrel are evenly distributed. Moreover, the lag screw 22 provides a robust structure with only minor material removed for the recesses 50 and 52, whether the pin 28 is used or omitted.

I claim:

1. A compression hip screw for fixation of a femoral head in a femur, the compression hip screw comprising a plate adapted for attachment to the femur, the plate including a barrel extending into an opening, the opening being formed in the femur and the femoral head, the barrel defining a bore extending therethrough, a first member coupled to the femoral head and extending into the barrel bore, a second member cooperating with the first member to oppose withdrawal of the barrel from the opening, and locking means cooperating with the first member and the barrel to limit rotation between the barrel and the first member, characterized in that the barrel defines an inferior side adjacent the portion of the plate attached to the femur and a superior side remote from the plate portion, the locking means comprising a groove defined in the barrel on the inferior side and a pin disposed in the groove, the pin extending into the barrel bore, and the first member defining a recess for receiving the pin whereby the pin forms an interference fit with the first member and the barrel whereby rotation is limited therebetween.

2. The compression hip screw of claim 1 in which the first member is slotted at a first end and the recess aligns with the slot to extend therefrom.

3. The compression hip screw of claim 1 in which the barrel defines a shoulder in abutment with the second member and the groove extends from the shoulder to a proximal end of the barrel.

4. The compression hip screw of claim 1 in which the barrel defines means disposed substantially at a proximal end of the barrel to yieldably retain the pin in the groove and the pin extends to the proximal end of the barrel in order to provide for alignment between the first member slot and the pin when the barrel and the pin are initially fitted over the first member.

5. The compression hip screw of claim 1 in which the groove forms the only interruption in a substantially uniform cylindrical surface for the barrel, and the barrel defines a constant radial thickness apart from the groove from the bore to an outer surface for the barrel.

6. The compression hip screw of claim 1 in which the first member recess extends from a first end which is slotted to an intermediate position on the first member not adjacent the threads whereby minimal material is removed from the first member to form the recess and accommodate the pin.

7. A compression hip screw for fixation of a femoral head in a femur bone, the compression hip screw comprising a plate adapted for attachment to the femur, the plate leading superiorly to a barrel extending into an opening, the opening being provided on the femur and the femoral head, a pair of members cooperating with the femoral head and the barrel to retain the femoral head connected to the femur and oppose withdrawal of the barrel from the opening, the barrel superior side being loaded in tension during a normal walking mode for the hip, the barrel inferior side being loaded in compression during a normal walking mode for the hip, and locking means cooperating with one of the pair of members and the barrel to oppose rotation between the one member and the barrel, the locking means cooperating with the barrel solely on the inferior side and substantially along a length of the barrel in order to provide a uniform cylindrical profile of constant radial thickness for the superior side of the barrel in the absence of holes through the radial thickness, whereby the tension imparted of the superior side of the barrel is spread evenly over the uniform cylindrical profile of constant radial thickness.

8. The compression hip screw of claim 7 in which the locking means comprises a pin extending into a groove formed by the barrel and a recess formed by the one member, the pin comprising a separate element from the barrel and the one member, and defining a diameter which extends substantially 75% in the groove and 25% in the recess.

9. The compression hip screw of claim 8 in which the one member is slotted at a distal end and the recess extends in a proximal direction from the slot.

10. The compression hip crew of claim 9 in which a pair of recesses extend in a proximal direction from the slot and the pin is compactly disposed within only one of the recesses.

11. In a compression hip crew for fixation of a femoral head in a femur, a plate adapted for attachment to the femur and including a barrel disposed within an opening formed in the femur, the barrel defining a bore therethrough for receiving a lag screw which threadably couples with the femoral head, a compression screw engageable with the lag screw and abutting the plate to oppose separation of the plate from the lag screw, and locking means cooperating with the lag screw and the barrel to prevent rotation therebetween, characterized in that the lag screw is slotted at a distal end with a pair of recesses extending substantially along the length of the lag screw, the barrel includes a single groove extending longitudinally on an inferior side, and the locking means comprises a pin separate from the barrel and disposed within one of the pair of recesses and within the single groove, the pin extending substantially over the length of the barrel to provide a robust interference between the lag screw and the barrel to prevent rotation and the pin being confined to the one recess and single groove for a compact arrangement between the lag screw and the barrel.

12. The compression hip screw of claim 11 in which the barrel defines a shoulder providing for abutment with the compression screw and the single groove extends from the shoulder to an opposite end of the barrel.

* * * * *